United States Patent [19]

Turnbull

[11] Patent Number: 5,184,611
[45] Date of Patent: Feb. 9, 1993

[54] TRACHEAL TUBE ASSEMBLIES AND LINERS

[75] Inventor: Christopher S. Turnbull, Kent, England

[73] Assignee: Smiths Industries Public Limited Company, London, England

[21] Appl. No.: 811,040

[22] Filed: Dec. 20, 1991

[30] Foreign Application Priority Data

Jan. 4, 1991 [GB] United Kingdom ............... 9100147

[51] Int. Cl.⁵ ............................................ A61M 16/00
[52] U.S. Cl. ........................ 128/207.14; 128/200.26; 128/912
[58] Field of Search ................. 128/200.26, 207.14, 128/207.15, 207.16, 911, 912

[56] References Cited

U.S. PATENT DOCUMENTS

| | | | |
|---|---|---|---|
| 4,646,733 | 3/1987 | Stroh et al. | 128/207.14 X |
| 4,817,598 | 4/1989 | LaBombard | 128/207.14 |
| 4,852,565 | 8/1989 | Eisele | 128/200.26 X |
| 4,909,248 | 3/1990 | McLennan et al. | 128/200.26 X |
| 5,052,386 | 10/1991 | Fischer, Jr. | 128/200.26 X |
| 5,062,420 | 11/1991 | Levine | 128/207.14 X |

FOREIGN PATENT DOCUMENTS

| | | |
|---|---|---|
| 1161720 | 2/1984 | Canada ........................... 128/207.14 |
| WO90/04992 | 5/1990 | PCT Int'l Appl. . |
| 2028139 | 8/1980 | United Kingdom . |
| 2056285 | 3/1981 | United Kingdom . |
| 2213384 | 8/1989 | United Kingdom . |
| 91/12844 | 9/1991 | World Int. Prop. O. . |
| 91-12845 | 9/1991 | World Int. Prop. O. . |

Primary Examiner—V. Millin
Assistant Examiner—Raleigh W. Chiu
Attorney, Agent, or Firm—Pollock, VandeSande and Priddy

[57] ABSTRACT

A tracheostomy tube assembly has a right-angle swivel connector connected to the machine end of a tracheostomy tube within which extends a liner. A fitment at the machine end of the liner has two annular collars between which several apertures open into the fitment. If the liner should be displaced rearwardly in the connector and the machine end of the liner becomes blocked, gas can flow through the apertures.

8 Claims, 1 Drawing Sheet

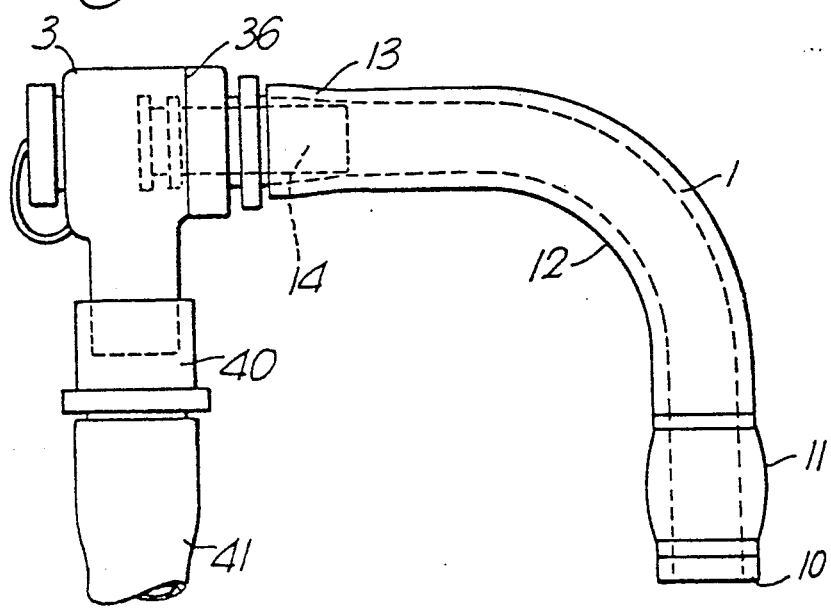
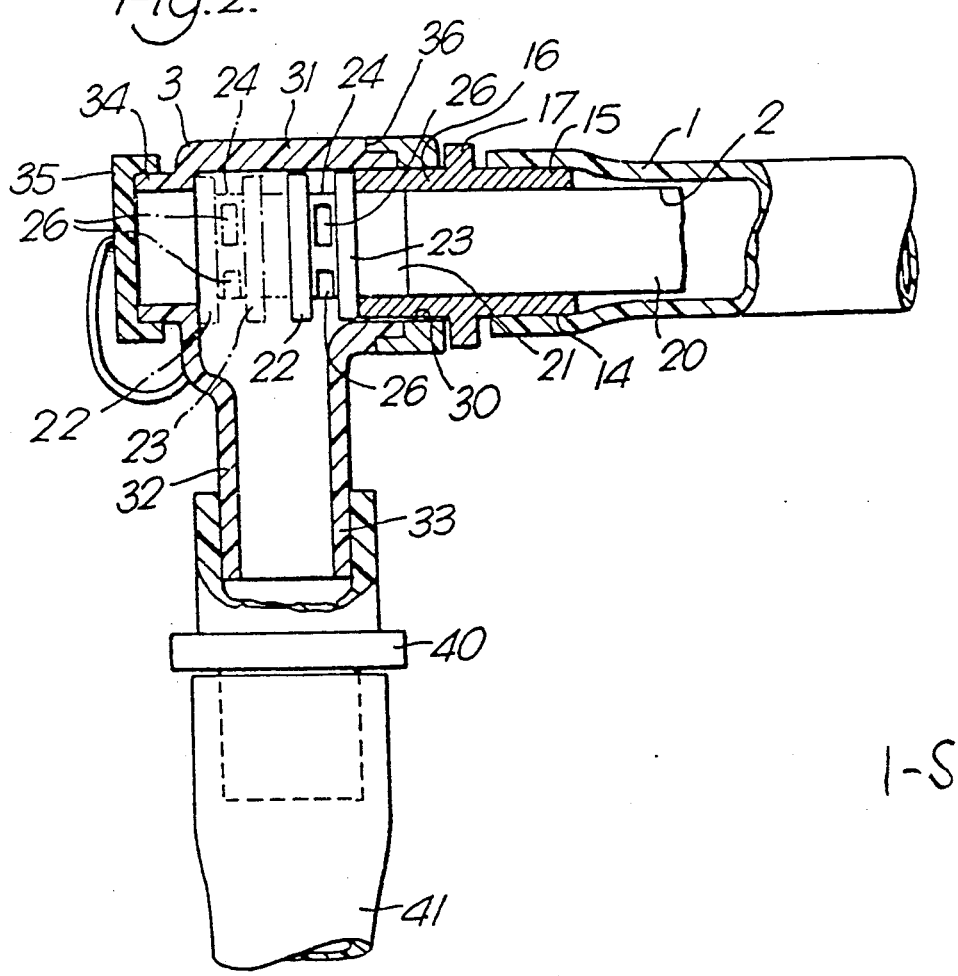

TRACHEAL TUBE ASSEMBLIES AND LINERS

BACKGROUND OF THE INVENTION

This invention relates to tracheal tube assemblies and liners for such assemblies.

Tracheal tubes are used to provide a gas passage to a patient's trachea. The patient end of the tube is inserted in the trachea and may be sealed with it by means of an inflatable cuff encircling the tube close to the patient end. The machine end of the tube extends out through the patient's mouth, in the case of an endotracheal tube, or through a surgically-made stoma in the patient's throat, in the case of a tracheostomy tube.

In use, secretions within the trachea and bronchii tend to build up on the bore through the tracheal tube, especially where the tube remains in place for a prolonged time, such as several days. This leads to problems in that the secretions can obstruct gas passage through the tube causing difficulties in breathing or ventilation. The secretions can also provide a site for the accumulation of bacteria which, if dislodged, can be inhaled by the patient and cause bronchial infection.

To reduce the adverse effects of this, it has been proposed to use a liner or inner tube which is inserted within the tracheal tube and which is removed and replaced by a fresh liner periodically. Tracheal tube assemblies including such liners have been described, for example in WO 91/12844 and WO 91/12845. The liner usually has a fitment at its machine end which is located with the machine end coupling on the tracheal tube and may be held in place by the mating coupling on ventilation tubing coupled to the tracheal tube. These connectors may be of the straight-through kind in which the ventilation tube is coupled coaxially of the machine end of the tracheal tube. Alternatively, the connector may be right-angled so that the ventilation tubing is led away at right angles to the machine end of the tracheal tube. The right-angle connector has advantages in that ventilation tubing can lie close to the patient, leading to a reduction in the force exerted on the tracheostomy or mouth by the weight of the tubing. Also, the right-angle connector can have an axial port enabling the introduction of a suction catheter, as required, into the bronchii.

Where the right-angle connector, the tracheal tube and its liner are made by the same manufacturer, to conform with one another, provision is made to retain the liner in its correct position. However, it is often the case that the connector will be made by a different manufacturer and that the liner will, therefore, not be held firmly in the tracheal tube by the connector. This leads to the risk that the liner may move rearwardly along the tracheal tube, such as on a sudden exhalation, and project into the connector, causing the right-angle port to be blocked either completely or to such an extent that breathing is severely impaired.

BRIEF SUMMARY OF THE INVENTION

It is an object of the present invention to provide a tracheal tube liner that can be used safely with different, angled connectors.

According to one aspect of the present invention there is provided a tracheal tube assembly including a tracheal tube, an angled connector having a side port and being mounted on the machine end of the tube, and a liner extending within the tube, the liner having a machine end which is open and is located within the angled connector so that gas can normally flow into the liner through the open machine end, and the liner additionally having a lateral aperture through which gas can flow in the event of the machine end of the liner being blocked.

The liner may comprise a flexible tube and a machine end fitment, the fitment being located within the angled connector. The lateral aperture is preferably in the machine end fitment. The machine end fitment may have two external annular collars, the lateral aperture being located between the collars. The angled connector may have a normally-closed port which is aligned with the machine end of the tube. The connector may be rotatable relative to the machine end of the tube. The tube may be a tracheostomy tube and have a substantially right angle bend.

According to another aspect of the present invention there is provided a liner according to the above one aspect of the invention.

A tracheostomy tube assembly including a liner, in accordance with the present invention, will now be described, by way of example, with reference to the accompanying drawing.

BRIEF DESCRIPTION OF THE DRAWING

FIG. 1 is a side elevation view of the assembly; and

FIG. 2 is a sectional side elevation to a larger scale of a part of the assembly.

DESCRIPTION OF THE PREFERRED EMBODIMENTS

The tracheostomy tube assembly comprises a tracheostomy tube 1, a liner 2, and a right-angle swivel connector 3.

The tube 1 is conventional with a patient end 10 for location within the trachea, and a cuff 11 encircling the tube close to its patient end. The cuff 11 can be inflated via an inflation lumen (not shown) to seal the tube with the trachea. The tube has a right angle bend 12 and extends to a machine end 13 which, in use, projects from the patient's neck through a surgical opening, or stoma, formed into the trachea. Inserted within the machine end 13 of the tube 1 is a male tapered patient end 15 of a straight coupling 14 which also has a male luer tapered machine end 16. The two ends 15 and 16 are separated by an external flange 17 which may have slots (not shown) to receive a tape by which the tube is held in place about the patient's neck. The machine end of the coupling 14 is adapted to couple with the female bore of a ventilation coupling 40 either directly, or, as in the present example, via the right-angle connector 3.

The right-angle connector 3 is also conventional, having a female luer taper coupling 30 at its patient end, a main body 31 with a hollow interior leading to a side port 32 that extends at right-angles to the patient coupling 30. The side port 32 has a male coupling 33 which receives, in use, the female anaesthetic or ventilation coupling 40 connected to the end of anaesthetic or ventilation tubing 41. The right-angle connector 3 also has a suction port 34 which is located axially in line with the patient coupling 30 and tube 1 and which is normally closed by a removable cap 35. The suction port 34 can be opened by removing the cap 35 to allow a suction catheter to be inserted via the tube 1 into the patient's bronchii, for removing secretion that collect there. The patient connector 30 is mounted with the body 31 of the connector 3 by means of a swivel joint 36 so that the machine coupling 33 can be rotated relative to patient end 30 at any desired angle.

The liner 2 comprises a thin-walled flexible tube 20 and a machine end fitment 21 sealed to the machine end of the tube 20. The length of the liner 2 is such that it extends to the patient end of the tracheostomy tube 1, and its external diameter is such that it is a close sliding fit within the tracheostomy tube. The machine end fitment 21 is more rigid than the tube 20 and is of generally cylindrical shape with open ends and with two external annular collars 22 and 23. The first collar 22 is located at the machine end of the fitment and the second collar 23 is separated from the first collar by a neck region 24 about 5 mm in length. The external diameter of both collars 22 and 23 is approximately equal to the external diameter of the machine end 16 of the coupling 14, the second collar 23 abutting the machine end of the coupling when the liner 2 is fully inserted in the tube 1. Around the neck region 24 between the two collars 22 and 23, there are three apertures or windows 26 (only two of which are visible) equally spaced from one another. The apertures 26 open into the interior of the fitment 21 so that gas is free to flow through them.

In normal use, the liner 2 is inserted in the tube 1 to its full extent, to the position shown by the solid lines in FIG. 2, with the second collar 23 against the coupling 14. Ventilation gas can, therefore, flow freely from the tube 41 via the right-angle connector 3 and into the liner 2 through the open machine end of its fitment 21. Gas can then flow along the tracheostomy tube 1 through the liner 2 and exit at the patient end 10 of the tube into the trachea. The liner 2 can be periodically removed by disconnecting the right-angle connector 3 from the tube 1, gripping the liner by the first collar 22 and pulling it out of the tube. A new liner is then pushed into the tube 1 and the coupling 3 replaced.

In some circumstances, such as on coughing or sudden exhalation, it is possible for the liner 2 to be dislodged rearwardly to the position shown by the broken lines in FIG. 2, in which the open machine end of the fitment 21 is in contact with the internal wall of the connector 3. With conventional liners, this would either prevent, or severely reduce the amount of, air flowing along the liner and hence along the tube 1 itself. With the liner 2 of the present invention, however, gas can still flow freely along the liner through the apertures 26 in the fitment 21.

It will be appreciated that the right-angle connector 3 itself could have an internal flange or the like to engage the rear end of the liner and prevent it becoming dislodged. The present invention, however, enables the liner to be used safely with couplings without any such provision for preventing dislodgement.

The liner could have a different number of apertures and they need not be located between two collars as described. For example, the apertures could be provided by castellations around the machine end of the fitment. Alternatively, the apertures could be located in the tube 20 of the liner.

What is claimed is:

1. A tracheal tube assembly including a tracheal tube having a patient end and a machine end, an angled connector having a side port and being mounted on the machine end of the tube, and a removable liner extending within the tracheal tube, the liner having an open machine end which is located within the angle connector so that gas can normally flow into the liner through the open machine end, the liner additionally having at least one lateral aperture located in the angled connector close to the machine end of the liner through which gas can flow if the machine end of the liner is blocked.

2. A tracheal tube assembly according to claim 1, wherein the liner comprises a flexible tube having a machine end fitment that is located within the angled connector.

3. A tracheal tube assembly according to claim 2, wherein the lateral aperture is in the machine end fitment of the liner.

4. A tracheal tube assembly according to claim 2 or 3, wherein the machine end fitment of the liner has two external annular collars, and wherein the lateral aperture is located between said collars.

5. A tracheal tube assembly according to claim 1, wherein the angled connector has a normally-closed port which is aligned with the machine end of the tracheal tube.

6. A tracheal tube assembly according to claim 1, wherein the angled connector is rotatable relative to the machine end of the tracheal tube.

7. A tracheal tube assembly according to claim 1, wherein the tracheal tube is a tracheostomy tube and has a substantially right angle bend.

8. A tracheal tube assembly comprising: a tracheal tube having a patient end and a machine end; an angled connector mounted on the machine end of the tracheal tube, the angled connector having a normally-closed port aligned with the machine end of the tube and a side port at substantially right angles to the normally-closed port; and a liner extending within the tracheal tube and comprising a thin-walled flexible tube having a machine end fitment attached thereto, said liner fitment being located within the angled connector and having an open machine end and a lateral aperture such that gas can normally flow through the open machine end of the liner fitment but, if said open machine end of said liner fitment should be blocked, gas can flow through said lateral aperture of said liner fitment.

* * * * *